(12) United States Patent
Chace

(10) Patent No.: US 7,297,545 B2
(45) Date of Patent: Nov. 20, 2007

(54) CLINICAL METHOD FOR THE GENETIC SCREENING OF NEWBORNS USING TANDEM MASS SPECTROMETRY AND INTERNAL STANDARDS THEREFOR

(75) Inventor: Donald H. Chace, Upper St. Clair, PA (US)

(73) Assignee: Pediatrix Screening, Inc., Bridgeville, PA (US)

( * ) Notice: Subject to any disclaimer, the term of this patent is extended or adjusted under 35 U.S.C. 154(b) by 311 days.

(21) Appl. No.: 11/169,158

(22) Filed: Jun. 28, 2005

(65) Prior Publication Data

US 2006/0008922 A1    Jan. 12, 2006

Related U.S. Application Data

(63) Continuation-in-part of application No. 10/252,115, filed on Sep. 23, 2002, now Pat. No. 7,011,977, which is a continuation-in-part of application No. 09/464,132, filed on Dec. 16, 1999, now Pat. No. 6,455,321, which is a continuation-in-part of application No. 09/277,119, filed on Mar. 26, 1999, now Pat. No. 6,258,605.

(60) Provisional application No. 60/117,880, filed on Jan. 30, 1999.

(51) Int. Cl.
    *G01N 31/00*    (2006.01)
(52) U.S. Cl. .................................. 436/8; 252/408.1
(58) Field of Classification Search .............. 436/8; 252/408.1
    See application file for complete search history.

(56) References Cited

U.S. PATENT DOCUMENTS

| 4,224,031 A | 9/1980 | Mee et al. |
| 5,072,115 A | 12/1991 | Zhou |
| 5,206,508 A | 4/1993 | Alderice et al. |
| 5,251,126 A | 10/1993 | Kahn et al. |

(Continued)

OTHER PUBLICATIONS

Perkin Elmer Brochure entitled "Amino Acid and Acylcarnitine Detection with the PerkinElmer Ms/MS System for Newborn Screening", Oct. 2005.*

(Continued)

*Primary Examiner*—Maureen M. Wallenhorst
(74) *Attorney, Agent, or Firm*—Charles E. Lyon; Brenda Herschbach Jarrell; Choate, Hall & Stewart, LLP

(57) ABSTRACT

A method for screening newborns using electrospray tandem mass spectrometry. The method improves the current protocols that use tandem mass spectrometry by assuring accurate and consistent results at the clinical level through enhanced quality controls and quality assurance protocols as applied to the scan profiling and sample preparation of blood spots from newborns. Specific additives are used in precise concentrations of internal standards, employing detailed controls adapted to distinguish twenty metabolites, which are scanned and vigorously compared to known spectra results. Revealing peaks, metabolite concentration, and scan intensities in the quality assurance steps are then compared to a range of thresholds to determine whether or not the sample is contaminated, drug-ridden, diagnosable, or unacceptable. All spectra results and quality assurance flags are organized in spreadsheet form and exported to a database where values are compiled and stored for daily output results and trend analysis. The method provides for high-throughput and quality results, having a consistent predictability for genetically testing newborns efficiently and accurately.

13 Claims, 14 Drawing Sheets

| INTERNAL STANDARD | Concentration (nmol/ml) | | Concentration (nmol/ml) |
|---|---|---|---|
| $^2H_9$-carnitine (free carnitine,CN) | 152 | | 0.76 |
| $^2H_3$ - acetylcarnitine (C2) | 38 | | 0.19 |
| $^2H_3$ - propionylcarnitine (C3) | 7.6 | | 0.04 |
| $^2H_3$ - butyrylcarnitine (C4) | 7.6 | | 0.04 |
| $^2H_9$ - isovalerylcarnitine (C5) | 7.6 | | 0.04 |
| $^2H_3$ - octanoylcarnitine (C8) | 7.6 | | 0.04 |
| $^2H_9$ - myristoylcarnitine (C14) | 7.6 | | 0.04 |
| $^2H_3$ - palmitoylcarnitine (C16) | 15.2 | | 0.08 |

20b / 22b

U.S. PATENT DOCUMENTS

| | | | |
|---|---|---|---|
| 5,252,489 | A | 10/1993 | Macri |
| 5,316,917 | A | 5/1994 | Roe |
| 5,352,891 | A | 10/1994 | Monning et al. |
| 5,365,426 | A | 11/1994 | Siegel et al. |
| 5,453,613 | A | 9/1995 | Gray et al. |
| 5,538,897 | A | 7/1996 | Yates et al. |
| 5,545,895 | A | 8/1996 | Wright et al. |
| 5,629,210 | A | 5/1997 | Hercules et al. |
| 5,878,746 | A | 3/1999 | Lemelson et al. |
| 6,258,605 | B1 | 7/2001 | Chace |
| 6,335,369 | B1 | 1/2002 | Cavazza |
| 6,429,230 | B1 | 8/2002 | Cavazza |
| 6,455,321 | B1 | 9/2002 | Chace |
| 6,653,349 | B1 | 11/2003 | Cavazza |
| 6,696,492 | B1 | 2/2004 | Cavazza |
| 6,696,493 | B2 | 2/2004 | Cavazza |
| 7,011,977 | B2 * | 3/2006 | Chace et al. .................. 436/86 |
| 2003/0199102 | A1 * | 10/2003 | Ostrup ....................... 436/173 |

OTHER PUBLICATIONS

C.G. Costa, et al., "Quantitative Analysis of Plasma Acylcarnitines Using Gas Chromatography Chemical Ionization Mass Fragmentometry," Journal of Lipid Research, vol. 38, pp. 173-182 (1997).

Y. Shigematsu, et al., "Modifications in Electrospray Tandem Mass Spectrometry for a Neonatal-Screening Pilot Study in Japan," Journal of Chromatography B, vol. 731, pp. 97-103 (1999).

K. Heinig, et al., "Determination of Carnitine and Acylcarnitines in Biological Samples by Capillary Electrophoresis-Mass Spectrometry," Journal of Chromatography B, vol. 735, pp. 171-188 (1999).

B.M. Kelly et al., "Electrospray Mass Spectra of Medium-Chain and Long-Chain Acylcarnitines," Organic Mass Spectrometry, vol. 27, pp. 924-926 (1992).

M.S. Rashed, et al., "Inborn Errors of Metabolism Diagnosed in Sudden Death Cases by Acylcarnitine Analysis of Postmortem Bile," Clinical Chemistry, vol. 41 (8), pp. 1109-1114 (1995).

J.A. Montgomery, et al., "Measurement of Urinary Free and Acylcarnitines: Quantitative Acylcarnitine Profiling in Normal Humans and in Several Patients with Metabolic Errors," Analytical Biochemistry, vol. 176 (1), pp. 85-95 (1989).

Chemical Abstracts, vol. 128 (19), p. 323 , Abstract No. 228108p (1998), F. Inoue, et al., "Analysis of Dried Blood Spots by Electrospray Mass Spectrometry," Bull. Kyoto Univ. Educ., Ser. B, vol. 91, pp. 15-22 (1997).

Chemical Abstract, vol. 123 (19), p. 508, Abstract No. 250402y (1995), M.S. Rashed, et al., "Diagnosis of Inborn Errors of Metabolism from Blood Spots by Acylcarnitines and Amino Acids Profiling Using Automated Electrospray Tandem Mass Spectrometry," Pediatr. Res., vol. 38(3), pp. 324-331 (1995).

Chemical Abstract, vol. 124 (5), p. 608 , Abstract No. 49898s (1996), N. Terada, et al., "Amino Acids and Acylcarnitines Analysis by ESIMS/MS" Nippon Iyo Masu Supekutoru Gakkai Koenshu, vol. 20, pp. 39-44 (1995).

Chemical Abstract, vol. 120 (13), p. 536 , Abstract No. 157900n (1994), M.S. Rashed, et al., "Electrospray Tandem Mass Spectrometry in the Diagnosis of Organic Acidemas," Rapid Commun. Mass Spectrom., vol. 8(1), pp. 129-133 (1994).

Rashed, et al., "Screening blood spots for inborn errors of metabolism by electrospray tandem mass spectrometry with a microplate batch process and a computer algorithm for automated flagging of abnormal profiles," Clinical Chem., vol. 43:7, pp. 1129-1141, (1997).

Nada, M., et al., "Investigation of Beta-Oxidation Intermediates in Normal MCAD-Deficient Human Fibroblasts Using Tandem Mass Spectrometry," Biochemical and Molecular Med., vol. 54, No. 1, pp. 59-66 (1995).

Chace, D., "Used of phenylalnine-to-tyrosine ratio determined by tandem mass spec . . . ," Clin. Chem., vol. 44:12 (1998).

Abdenur, J., et al., Diagnosis of Isovaleric Acidaemia by Tandem Mass Spectrometry: False Positive Result due to Pivaloyl Carnitine in a Newborn Screening Programme; J. Inher. Metab. Dis., vol. 21, pp. 624-630 (1998).

Abdenur, J., et al., "MCAD Deficiency: Acylcarnitines (AC) by Tandem Mass Spectrometry (MS-MS) are Useful to Monitor Dietary Treatment," Adv. Exp. Med. Biol., vol. 466, pp. 353-363 (1999).

Albers, S., et al., "Detection of Neonatal Carnitine Palmitoyltransferase II Deficiency by Expanded Newborn Screening with Tandem Mass Spectrometry," Pediatrics 2001; 107:E103.

Barns, R., et al., "Carnitine in Dried Blood Spots: A Method Suitable for Neonatal Screening," Clin. Chim. Acta, vol. 197, pp. 27-33 (1991).

Chace, D., et al, "Errors Caused by the Use of D,L-octanoly Carnitine for Blood-Spot Calibrators," Clin. Chem. vol. 47, pp. 758-760 (2001).

Clayton, P., et al, "Screening for Medium Chain Acyl-coA Dehydrogenase Deficiency using Electrospray Ionisation Tandem Mass Spectrometry," Arch. Dis. Child, vol. 79, pp. 109-115 (1998).

Gaskell, S., et al., "Differentation of Isomeric Acylcarnitines using Tandem Mass Spectrometry," Anal. Chem., vol. 58, pp. 2801-2805 (1986).

Gempel, K., et al., "Adult Carnitine Palmitoyltranferase II Deficiency: Detection of Characteristic Carnitine Esters in Serum by Tandem Mass Spectrometry," J. Inherit. Metab. Dis., vol. 22, pp. 941-942 (1999).

Johnson, A., et al., "The Use of Automated Electrospray Ionization Tandem MS for the Diagnosis of Inborn Errors of Metabolism from Dried Blood Sports," Biochem. Soc. Trans., vol. 24, pp. 932-938 (1996).

Johnson, D., "Inaccurate Measure of Free Carnitine by the Electrospray Tandem Mass Spectrometry Screening Methods for Blood Spots," J. Inher. Metab. Dis., vol. 22, pp. 201-202 (1999).

Kodo, N., et al., "Quantitative Assay of Free and Total Carnitine using Tandem Mass Spectrometry," Clin. Chim. Acta, vol. 186, pp. 383-390 (1989).

Liberato, D., et al., "Analysis of Acylcarnitine s in Human Metabolic Disease by Thermospray Liquid Chromatography/Mass Spectrometry," Burlingame A.A. Castagnoli N., editors, Mass Spectrometry in the Health and Life Sciences, Amsterdam, NL; Elsevier Science Publishers, pp. 333-348 (1958).

Millington, D., et al., "Application of Fast Atom Bombardment with Tandem Mass Spectrometry and Liquid Chromatography/Mass Spectrometry to the Analysis of Acylcarnitines in Human Urine, Blood and Tissue," Anal. Biochem., vol. 180, pp. 331-339 (1989).

Millington, D., et al., "Tandem Mass Spectrometry: A New Method for Acylcarnitine s Profiling with Potential for Neonatal Screening for Inborn Errors of Metabolism," J. Inher. Dis., vol. 13, pp. 321-324 (1990).

Stevens, R., et al., "Assay for Free and Total Carnitine in Human Plasma Using Tandem Mass Spectrometry," Clin. Chem., vol. 46, pp. 727-729 (2000).

Vreken, P., et al., "Quantitative Plasma Acylcarnitine Analysis Using Electrospray Tandem Mass Spectrometry for the Diagnosis of Organic Acidaemias and Fatty Acid Oxidation Defects," J. Inher. Metab. Dis., vol. 22, pp. 302-306 (1999).

Willey, V., et al., "Newborn Screening with Tandem Mass Spectrometry; 12 Months' Experience in NSW Australia," Acta Paediatr Suppl., vol. 88, pp. 48-51 (1999).

Yergey, A., et al., "Thermospray Liquid Chromatography/ Mass Spectrometry for the Analysis of L-Carnitine and its Short-Chain Acyl Derivatives," Anal Biochem., vol. 139, pp. 278-283 (1984).

Savica, et al., "Plasma & Muscle Carnitine Levels in Haemodialysis Patients with Morphological-Ulstructural Examination of Muscle Samples," Nephron, vol. 35, pp. 232-236 (1983).

Rodriguez-Segade, et al., "Carnitine deficiency in haemodialysed patients," Clinical Chimica Acta, vol. 59, pp. 249-256 (1986).

Rodriguez-Segade, et al., "Carnitine concentrations in dialysed and undialysed patients with chronic renal insufficiency," Ann. Clinical Biochemistry, vol. 23, pp. 671-675 (1986).

Millington, D., et al; Diagnosis of Metabolic Disease, *Biological Mass Spectrometry: Present and Future*, 1994; pp. 559-579.

Millington, D., et al; Carnitine and Acylcarnitines in Metabolic Disease Diagnosis and Management; *Mass Spectrometry: Clinical and Biomedical Applications*, vol. 1; 1992; pp. 299-318.

Millington, D., et al; The Analysis of Diagnostic Markers of Genetic Disorders in Human Blood and Urine using Tandem Mass Spectrometry with Liquid Secondary Ion Mass Spectrometry; *International Journal of Mass Spectrometry and Ion Processes, 111*; 1991; pp. 211-228.

Van Hove, J., et al; Medium-Chain Acyl-CoA Dehydrogenase (MCAD) Deficiency: Diagnosis by Acylcarnitine Analysis in Blood; *Am. J. Hum. Genet. S2*; pp. 958-966.

Chace, D., et al; Rapid Diagnosis of Maple Syrup Urine Disease in Blood Spots from Newborns by Tandem Mass Spectrometry; *Clinical Chemistry*, vol. 41 (1); 1995; pp. 62-68.

Chace, D., et al; Rapid Diagnosis of Homocystinuria and Other Hypermethioninemias from Newborns' Blood Spots by Tandem Mass Spectrometry; *Clinical Chemistry*, vol. 42 (3); 1996; pp. 349-355.

Chace, D., et al; Rapid Diagnosis of Phenylketonuria by Quantitative Analysis for Phenylalanine and Tyrosine in Neonatal Blood Spots by Tandem Mass Spectrometry; *Clinical Chemistry*, vol. 39, (1); 1993; pp. 66-71.

Chace, D., et al; Rapid Diagnosis of MCAD Deficiency: Quantitative Analysis of Octanoylcarnitine and Other Acylcarnitines in Newborn Blood Spots by Tandem Mass Spectrometry; *Clinical Chemistry*, vol. 43 (11); 1997; pp. 2106-2113.

Chace, D., et al; Neonatal Screening for Inborn Errors of Metabolism by Automated Dynamic Liquid Secondary Ion Tandem Mass Spectrometry; *New Horizons in Neonatal Screening*; 1994; pp. 373-375.

Van Hove, J., et al; Acylcarnitines in Amniotic Fluid: Application to the Prenatal Diagnosis of Propionic Acidaemia; *J. Inher. Metab. Dis* 16; 1993; pp. 361-367.

Van Hove, J., et al; Intravenous L-Carnitine and Acetyl-L-Carnitine in Medium-Chain Acyl-Coenzyme A Dehydrogenase Deficiency and Isovaleric Acidemia; *Pediatric Research*, vol. 35 (1); 1994; pp. 96-101.

Shigematsu, Y., et al; Prenatal Diagnosis of Organic Acidemias Based on Amniotic Fluid Levels of Acylcarnitines; *Pediatric Research*, vol. 39 (4); 1996; pp. 680-683.

Chace, D., et al; Expansion of Newborn Screening Programs Using Automated Tandem Mass Spectrometry; *MRDD Research Reviews*, vol. 5; 1999; pp. 150-154.

Chace, D., et al; Validation of Accuracy-based Amino Acid Reference Materials in Dried-Blood Spots by Tandem Mass Spectrometry for Newborn Screening Assays; *Clinical* Chemistry, vol. 45, (8); 1999; pp. 1269-1277.

Chace, D., et al; Laboratory Integration And Utilization Of Tandem Mass Spectrometry In Neonatal Screening: A Model For Clinical Mass Spectrometry In The Next Millennium; *Acta Paediatr Supp.*, vol. 432; 1999; pp. 45-47.

Andresen, B., et al; Medium-Chain Acyl-CoA Dehydrogenase (MCAD) Mutations Identified by MS/MS-Based Prospective Screening of Newborns Differ from Those Observed in Patients with Clinical Symptoms: Identification and Characterization of a New, Prevalent Mutation that Results in Mild MCAD Deficiency; *Am. J. Hum. Genet. 68*; 2001; pp. 1408-1418.

Naylor, E., et al; Automated Tandem Mass Spectrometry for Mass Newborn Screening for Disorders in Fatty Acid, Organic Acid, and Amino Acid Metabolism; *Journal of Child Neurology*, vol. 14, Supplement 1; Nov. 1999; pp. 84-88.

Adam, B., et al; Recoveries of Phenylalanine from Two Sets of Dried-Blood-Spot Reference Materials: Prediction from Hematocrit, Spot Volume, and Paper Matrix; *Clinical Chemistry* 46 (1); 2000; pp. 126-128.

Kao, P., et al; Diagnosis of Adrenal Cortical Dysfunction by Liquid Chromatography-Tandem Mass Spectrometry; *Annals of Clinical & Laboratory Science*, vol. 31 (2); 2001; pp. 199-204.

Chace, D., et al; Errors Caused by the Use of D,L-Octanoylcarnitine for Blood-Spot Calibrators; *Clinical Chemistry* 47 (4); 2001; pp. 758-760.

Chace, D., et al., Electrospray Tandem Mass Spectrometry for Analysis of Acylcarnitines in Dried Postmortem Blood Specimens Collected at Autopsy from Infants with Unexplained Cause of Death; *Clinical Chemistry*, vol. 47 (7); 2001; pp. 1166-1182.

Chace, D., et al; Rapid Diagnosis of Methylmalonic and Propionic Ademias: Quantitative Tandem Mass Spectrometric Analysis of Propionylcarnitine in Filter-Paper Blood Specimens Obtained from Newborns; *Clinical Chemistry* 47; 2001; pp. 2040-2044.

Chace, D., Mass Spectrometry in the Clinical Laboratory; *Chemical Reviews*, 2001, vol. 101; pp. 455-477.

Chace, D., et al; Neonatal Blood Carnitine Concentrations: Normative Data by Electrospray Tandem Mass Spectometry; *Pediatric Research*, vol. 53 (5); 2003; pp. 823-829.

Chace, D., Mass Spectrometry-based Diagnostics: The Upcoming Revolution in Disease Detection Has Already Arrived; *Clinical Chemistry* 49 (7); 2003; pp. 1227-1228.

Chace, D., Measuring Mass: From Positive Rays to Proteins; *Clinical Chemistry* 49; 2003; pp. 342-343.

Seymour C.A., et al., "Newborn Screening for Inborn Errors of Metabolism: A Systematic Review", Health Technology Assessment (1997), v. 1, No. 11, pp. 1-97.

The Supplementary European Search Report (EP00947150) (3 pp).

* cited by examiner

| | 20a | | 22a |
|---|---|---|---|
| INTERNAL STANDARD | Concentration (umol/L) | | Concentration (umol/L) |
| $^{15}N, 2-^{13}C$-Glycine | 2500 | | 12.5 |
| $^2H_4$ - Alanine | 500 | | 2.5 |
| $^2H_8$ - Valine | 500 | | 2.5 |
| $^2H_3$ - Leucine | 500 | | 2.5 |
| $^2H_3$ - Methionine | 500 | | 2.5 |
| $^2H_5$ - Phenylalanine | 500 | | 2.5 |
| $^2H_4$ - Tyrosine | 500 | | 2.5 |
| $^2H_3$ - Aspartate | 500 | | 2.5 |
| $^2H_3$ - Glutamate | 500 | | 2.5 |
| $^2H_2$ - Ornithine 2HCl | 500 | | 2.5 |
| $^2H_2$ - Citrulline | 500 | | 2.5 |
| $^2H_4,^{13}C$ - Arginine HCl | 500 | | 2.5 |

FIG. 2a

| | 20b | | 22b |
|---|---|---|---|
| INTERNAL STANDARD | Concentration (nmol/ml) | | Concentration (nmol/ml) |
| $^2H_9$-carnitine (free carnitine, CN) | 152 | | 0.76 |
| $^2H_3$ - acetylcarnitine (C2) | 38 | | 0.19 |
| $^2H_3$ - propionylcarnitine (C3) | 7.6 | | 0.04 |
| $^2H_3$ - butyrylcarnitine (C4) | 7.6 | | 0.04 |
| $^2H_9$ - isovalerylcarnitine (C5) | 7.6 | | 0.04 |
| $^2H_3$ - octanoylcarnitine (C8) | 7.6 | | 0.04 |
| $^2H_9$ - myristoylcarnitine (C14) | 7.6 | | 0.04 |
| $^2H_3$ - palmitoylcarnitine (C16) | 15.2 | | 0.08 |

FIG. 2b

| C4OH | C6 | C5OH | Benzoyl CN | C8OH | C8:1 | C8 | C8OH(C3DC) |
|---|---|---|---|---|---|---|---|
| 1 | 0.32 | 0.9 | 1 | 0.5 | 0.8 | 0.35 | 0.32 |
| 0.11 | 0.05 | 0.03 | 0.01 | 0.04 | 0.04 | 0.03 | 0.02 |
| 0.12 | 0.02 | 0.14 | 0.03 | 0.02 | 0.1 | 0.05 | 0.02 |

| C10:2 | C10:1 | C10 | C4DC | C5DC(C10OH) | C12:1 |
|---|---|---|---|---|---|
| 0.32 | 0.32 | 0.42 | 0.8 | 0.14 | 0.75 |
| 0.05 | 0.4 | 0.02 | 0.14 | 0.02 | 0.08 |
| 0.07 | 0.8 | 0.09 | 0.3 | 0.03 | 0.06 |

| Full Path | Filename | Sample Name | Failed Tests | Free CN | Hydrofree |
|---|---|---|---|---|---|
|  |  | Upper Thresholds |  | 350 | 7.5 |
|  |  | Lower Thresholds |  | 10 |  |
| hardrive:de | ss900945 | Sciex-1 |  | 22.1 | 1.49 |
| hardrive:de | xgn99012 | Sciex-1 | Quality Control | 47.05 | 1.58 |

| C2 | C2Glutamate | C3mm | C3/C2 | C3 | C4 | C5:1 |
|---|---|---|---|---|---|---|
| 80 | 25 |  | 5 | 0.3 | 4.5 | 1.75 | 0.5 |
| 4 |  |  |  |  | 0.2 |  |  |
| 8.54 | 2.75 |  | 1.3 | 0.15 | 0.88 | 0.19 | 0.04 |
| 8.28 | 2.19 |  | 1.39 | 0.22 | 0.91 | 0.1 | 0.06 |

FIG. 3a

| C12 | C6DC | C12OH | C14:2 | C14:1 | C14 | C14OH | C16:1 | C16 |
|---|---|---|---|---|---|---|---|---|
| 0.9 | 0.25 | 0.25 | 0.4 | 1.1 | 1.3 | 0.25 | 1.5 | 10 |
| | | | | | | | | |
| 0.1 | 0.02 | 5.36E-03 | 0.03 | 0.14 | 0.99 | 7.15E-03 | 0.18 | 2.82 |
| 0.04 | 0.02 | 0.02 | 0.06 | 0.12 | 0.11 | 0.02 | 0.12 | 0.79 |

| C16OH | C18:2 | C18:1 | C18 | C12DC |
|---|---|---|---|---|
| 0.22 | 3 | 6 | 4 | 2 |
| | | | | |
| 0.02 | 0.11 | 1.31 | 0.98 | 0.16 |
| 0.02 | 0.33 | 1.45 | 0.61 | 0.12 |

| C18:1OH | C18OH | bad derivative | EDTA | C8 C3 | C3 C16 | C5DC C16 |
|---|---|---|---|---|---|---|
| 0.22 | 0.24 | 0.3 | | 0.2 | 1 | 2 | 0.12 |
| | | | | | | |
| 0.01 | 0.01 | 0.04 | | 0.02 | 0.03 | 0.31 | 8.79E-03 |
| 0.02 | 0.02 | 0.04 | | 0.15 | 0.06 | 1.16 | 0.03 |

| C14:1 C16 | C4 C3 | C8 IS INT | Gly | Ala | Val |
|---|---|---|---|---|---|
| 0.28 | 1.5 | | 750 | 1250 | 300 |
| | | 400 | | | |
| 0.05 | 0.22 | 2240 | 143.97 | 192.28 | 81.19 |
| 0.15 | 0.11 | 1430 | 250.72 | 341.21 | 132.6 |

FIG. 3a (cont.)

CLINICAL METHOD FOR THE GENETIC SCREENING OF NEWBORNS USING TANDEM MASS SPECTROMETRY AND INTERNAL STANDARDS THEREFOR

CROSS REFERENCE TO RELATED APPLICATIONS

This application is a continuation-in-part of U.S. Ser. No. 10/252,115 filed on Sep. 23, 2002 now U.S. Pat. No. 7,011,977, which is a continuation-in-part of U.S. Ser. No. 09/464,132 filed on Dec. 16, 1999, now U.S. Pat. No. 6,455,321, which is a continuation-in-part of U.S. Ser. No. 09/277,119 filed Mar. 26, 1999, now U.S. Pat. No. 6,258,605, which claims the benefit of provisional application U.S. Ser. No. 60/117,880 filed on Jan. 30, 1999. The disclosures of each of these cases is incorporated herein by reference in their entirety.

BACKGROUND OF THE INVENTION

1. Field of the Invention

The present invention relates to a high throughput, cost-effective, and low false-positive method of genetic screening, capable of performance over a wide range of metabolite groups, using electrospray tandem mass spectrometry. Efficient sample preparation and stringent quality controls are implemented as critical keys in maintaining consistency and accuracy in the resulting data for use in medical diagnosis.

2. Description of Prior Art

Mass spectrometry has been making significant contributions to the diagnosis of metabolic diseases for over 20 years. Fast Atom Bombardment Tandem Mass Spectrometry (FAB-MS/MS) analysis of acylcarnitines in very small volumes of whole blood or plasma has been previously made routine. See Millington, et al., Mass Spectrometry: Clinical and Biomedical Applications, 1, ch. 8, 299-318. It had been a very satisfactory biochemical method for the differential diagnosis of disorders of fatty acid catabolism, and the instrumental method recognized numerous defects of branched-chain amino acid catabolism. The frequency of occurrence of these diseases and their association with sudden, unexplained deaths has generated a great medical interest in the development of neonatal screening tests.

Routine analysis of amino acids and acylcarnitines by Liquid Secondary Ion Tandem Mass Spectrometry (LSIMS/MS) from blood spots on filter paper has been demonstrated previously as well. See Chace et al., "Neonatal Screening for Inborn Errors of Metabolism by Automated Dynamic Liquid Sewary Ion Tandem Mass Spectrometry New Horizons in Neonatal Screening, 1994. To increase the number and rate at which samples can be analyzed, the development of automated sample preparation, instrumental analysis, and data interpretation was required. The increase in sample throughput and the ease of sample preparation allows for the more efficient and exacting diagnosis of a great number of metabolic disorders, a process necessary in determining the health of a newborn baby, or, for that matter, anyone in clinical care. The ranges of clinical symptoms and abnormalities in simple blood tests are so extreme that extensive biochemical investigation is warranted whenever metabolic disease is suspected, as noted in Millington, et al., "Diagnosis of Metabolic Disease," from Biological Mass Spectrometry: Present and Future, 3.15, 1994.

Metabolic profiling of amino acids and acylcarnitines from blood spots by use of automated electrospray tandem mass spectrometry (ESI-MS/MS), is a more powerful diagnostic tool for inborn errors of metabolism. See Rashed, et al., Clinical Chem. 43:7, 1129-1141. New approaches to sample preparation and data interpretation have helped establish the methodology as a robust, high-throughput neonatal screening method. Compared with older methods, ESI-MS/MS is much more versatile and less labor intensive, because most of the steps can be automated.

Inborn errors of metabolism usually result from defective enzymes or cofactors. Medium-chain acyl-CoA dehydrogenase (MCAD) deficiency is a very common disorder of fatty acid oxidation. As seen in Chace et al., Clin. Chem., 43:11, 2106-2113, MCAD deficiency is diagnosed on the basis of the increase of medium chain length acylcarnitines, as identifiable by isotope dilution mass spectrometry methods. Butyl esters of acylcarnitines share a similar fragmentation pattern with a common fragment ion at 85 Da after collision-induced dissociation using a mass spectrometer. The fragmentation pattern differences are compared to known spectra of healthy individuals and thereby can be diagnosed. In a clinical setting, analysis of acylcarnitines by tandem mass spectrometry is possible as their associated methyl esters allow the diagnostic recognition of all patients with MCAD deficiency, regardless of the underlying mutation, symptomatic state, or treatment Also, the analysis of amino acids as their associated butyl esters has been validated for newborn screening of phenylketonuria (PKU), tyrosinemia, maple syrup urine disease, and homocystinuria, all of which, among others, are detected by mass spectrometry.

The most selective and sensitive spectrometry, as it relates to genetic disorders, is performed by the automated, electrospray tandem mass spectrometer. The use of ESI-MS/MS has been presented to successfully and quickly provide a specific and accurate screening method (Rashed, et al.). The method itself, however, must be complemented with an efficient sampling procedure and optimized injection and scan function mode to accommodate, with utmost accuracy, many samples at one time, thereby maximizing throughput while maintaining sensitivity and accuracy.

The efficiency of the ionization of the compounds is very high with the implementation of electrospray ionization. As seen in U.S. Pat. No. 5,352,891, Monning et al., the high ionization efficiency allows useful spectra required for even very small quantities of material. In other words, electrospray tandem mass spectrometry is very sensitive and specific in regards to its compound injection systems, thereby allowing a more broad spectrum of diseases to be covered, a lower false positive rate to be achieved, high specificity to be obtained, and shortened analytical time permitted. The use of the electrospray tandem MS/MS has been shown to increase throughput. Moreover, the technique has been successfully applied to prenatal diagnosis (Rashed, et al., 1130) and other screening processes. However, optimization of the method of screening newborns must be achieved by maximizing sample throughput in the most efficient and accurate way, beginning in the sample preparation, and culminating with the quality assurance. The overall process lends itself to parental peace-of-mind, and expedient and cost-effective results.

Sample preparation in support of the genetic screening of an individual for carnitines and .alpha.-amino acids (genetic markers for inborn errors in metabolism) for use in mass spectrometry is seen in the art. The standard method of collecting samples for neonatal screening is a heel prick followed by depositing the whole blood on special filter paper (or Guthrie cards) as a series of spots. See Millington, et al., International Journal of Mass Spectrometry and Ion Processes, 111, 212, 1991. The latest developed method of preparing the butyl ester derivatives of acylcarnitines and amino acids from the blood spots consists of processing samples in microplates. An automated blood-spot puncher punches a single blood spot from each Guthrie card directly into the individual wells of the microplate. To the blood spot punch in each well a methanolic solution containing known concentrations of stable isotope-labeled standards is added. The label standards might include glycine and alanine; valine, methionine, and phenylalanine; leucine and tyrosine; ornithine; carnitine; acetylcarnitine; propionylcarnitine; octanoylcarnitine; and palmitoylcarnitine, all in combination in some concentration as to enhance the sensitivity for particular compounds, as required by respective testing protocol. The samples are extracted and the extracts are then transferred to another microplate where the methanol is removed through evaporation. To the residue in each well, butanolic HCl or other chemical modifiers are added and the derivatization is completed by heating. Final residues are reconstituted and placed in an autosampler tray for introduction into the MS.

The incorporation of isotope-dilution techniques as standards provides quantitative information for specific components of each sample. There is the need for an optimal concentration of a combination of 12 amino acid standards and 8 acylcarnitinelcarnitine standards to improve accuracy and provide for quality control, as well as to provide for a number of scan functions that maximize metabolite information with high-throughput. Quality control and quality assurance in a clinical environment is of utmost importance because of the method and instrumentation that has evolved for the optimization of sample throughput. It is especially important as mass spectrometry results are correlated to the general populations of newborns so as to show accurate results in demographic trends.

The advantages of ESI-MS/MS over alternative methods of analysis are its high specificity and accuracy of quantification through use of the isotope-dilution technique, plus its speed and amenability to automation See Chace et al., Clin. Chem. Vol. 39, No. 1, 1993. Coupling the sensitivity in detection with the requirement that newborn screening requires rapid throughput, high accuracy, high precision, high selectivity, and a high value to low cost ratio, there is now a need in the clinical environment, now satisfied by the present invention, for an accurate means of assuring the quality of data for genetic disorder diagnosis is obtained in an organized and accurate manner. This quality can be coupled to the most efficient method of preparing and scanning samples, so as the number of false-positives and false-negatives are reduced, and sample throughput is necessarily maximized in the diagnostic clinical setting.

PRIOR ART

U.S. Pat. No. 5,538,897, Jul. 23, 1996 (Yates, III et al.) shows a method for correlating a peptide fragment mass spectrum with amino acid sequences derived from a database. A peptide is analyzed by a tandem mass spectrometer to yield a peptide fragment mass spectrum. A protein sequence database or a nucleotide sequence database is used to predict one or more fragment spectra for comparison with the experimentally derived fragment spectrum. The various predicted mass spectra are compared to the experimentally derived fragment spectrum using a closeness-of-fit measure, preferably calculated with a two-step process, including a calculation of a preliminary score and, for the highest-scoring predicted spectra, calculation of a correlation function.

U.S. Pat. No. 5,206,508 Apr. 27, 1993 (Alderdice et al.) teaches a tandem mass spectrometry system, capable of obtaining tandem mass spectra for each parent ion without separation of parent ions of differing mass from each other. This system would in addition provide the capability to select a particular ion prior to excitation.

U.S. Pat. No. 5,352,891, Oct. 4, 1994 (Monning et al.) demonstrates the production of mass spectra of chemical compounds of high molecular weights having a multiplicity of peaks is improved by generating an enhanced mass spectrum from the observed mass-to-charge spectrum. Signal-to noise ratio can in some applications be improved by including in the product all portions within the discrete peaks in the mass-to-charge spectrum, which are contained within a window around each of the discrete peaks.

SUMMARY OF THE INVENTION

It is the objective of the present invention to improve the method of screening newborns by implementing efficient sampling protocols and data quality controls. As initial and final steps to the use of electrospray tandem mass spectrometry for inborn metabolite error screening, the sample efficiency and quality assurance will complement a more rapid sample throughput method with a high value to low cost ratio. All values are compared to known thresholds as a means for evaluating the contents of the sample. High accuracy and high precision found in a large number of samples will quickly provide consistent diagnosis at the clinical level.

Electrospray tandem mass spectrometry is very sensitive and specific and can detect a broad spectrum of disorders at the genetic level. The already shortened analytical time and high specificity increases the rate at which samples that can be analyzed. Including internal standards in the sample preparation that decrease extraction error and allow for mixed mode scan functions further increases sample throughput The internal standards are used to provide the quantitative information needed to detect specific components. Use of proper ratios of each particular ion enables the detection of many metabolites at one time, thereby eliminating duplicate analysis, allowing secondary runs to be used for quality assurance and proficiency testing rather than for detection of preliminary compounds.

It is a secondary objective of the present method to include EDTA standards that can determine whether or not the blood was collected properly. Contaminated blood or blood collected from tubes rather than a heel prick spot is improper and identifiable by this standard.

It is a third objective of the present method to include quality assurance standards such as $^2H_3$-Serine (deuterium 3 labeled Serine) to show the computer is recognizing normally unfounded compounds. Serine is an amino acid that is not included or recognized in a normal scan, so $^2H_3$-Serine is added to an acylcarnitine scan to show that, when this compound is detected and shown as a peak, the computer is capable of detecting foreign compounds. In effect, drug-ridden or contaminated samples may be flagged.

It is a fourth objective of the present method to include proper correction factors, mass values, quality assurance flags, and sample preparation flags as input values, complementing a database that is used for checking calculations as produced using a spreadsheet, thereby insuring accurate data reduction. This provides enhanced quality assurance. When an abnormal sample is noted, a recommended action is to be taken. Database storage of values facilitates disease rate data reporting, trend generation and analysis, total sample-per-day values, and QA/QC analyses.

It is a fifth objective of the present method to include a quality control step that uses unlabeled standards and control blood standards to assure the consistency and accuracy in the detection of the twenty metabolites.

BRIEF DESCRIPTION OF THE DRAWINGS

Accordingly, the method generally comprises, after receiving a plurality of blood spots, combining an amino acid standard and a free carnitine/acylcarnitine standard to form an internal standard containing a plurality of labeled compounds. A plurality of samples are prepared wherein each of said samples comprise the internal standard, methanol, and a blood extract from one of the blood spots taken from the newborn baby. The samples are scanned using the electrospray tandem mass spectrometer to produce scan results. Control blood samples are then prepared and scanned, wherein each of said control blood contain hemolyzed blood, EDTA, $^2H_3$-Serine. A plurality of standards having hemolyzed blood, EDTA, $^2H_3$-Serine, and one of the labeled compounds is also prepared and scanned. Ultimately, the control sample results obtained for each of the quality control samples is compared to the plurality of standard results obtained for each of said standards. In this way, the data obtained for each newborn scan result is assured accuracy and consistency for any further action such as diagnosis or re-testing.

FIGS. 2a and 2b are listings of internal standards for amino acids and free carnitines/acylcarnitines.

FIG. 3a is a spreadsheet showing the possible upper or lower thresholds used to determine which samples are to be flagged for further decision-making or re-testing.

DETAILED DESCRIPTION OF THE PREFERRED EMBODIMENT

The method will now be described in detail in relation to a preferred embodiment and implementation thereof which is exemplary in nature and descriptively specific as disclosed. As is customary, it will be understood that no limitation of the scope of the invention is thereby intended The invention encompasses such alterations and further modifications in the illustrated device, and such further applications of the principles of the invention illustrated herein, as would normally occur to persons skilled in the art to which the invention relates.

Figure 1:
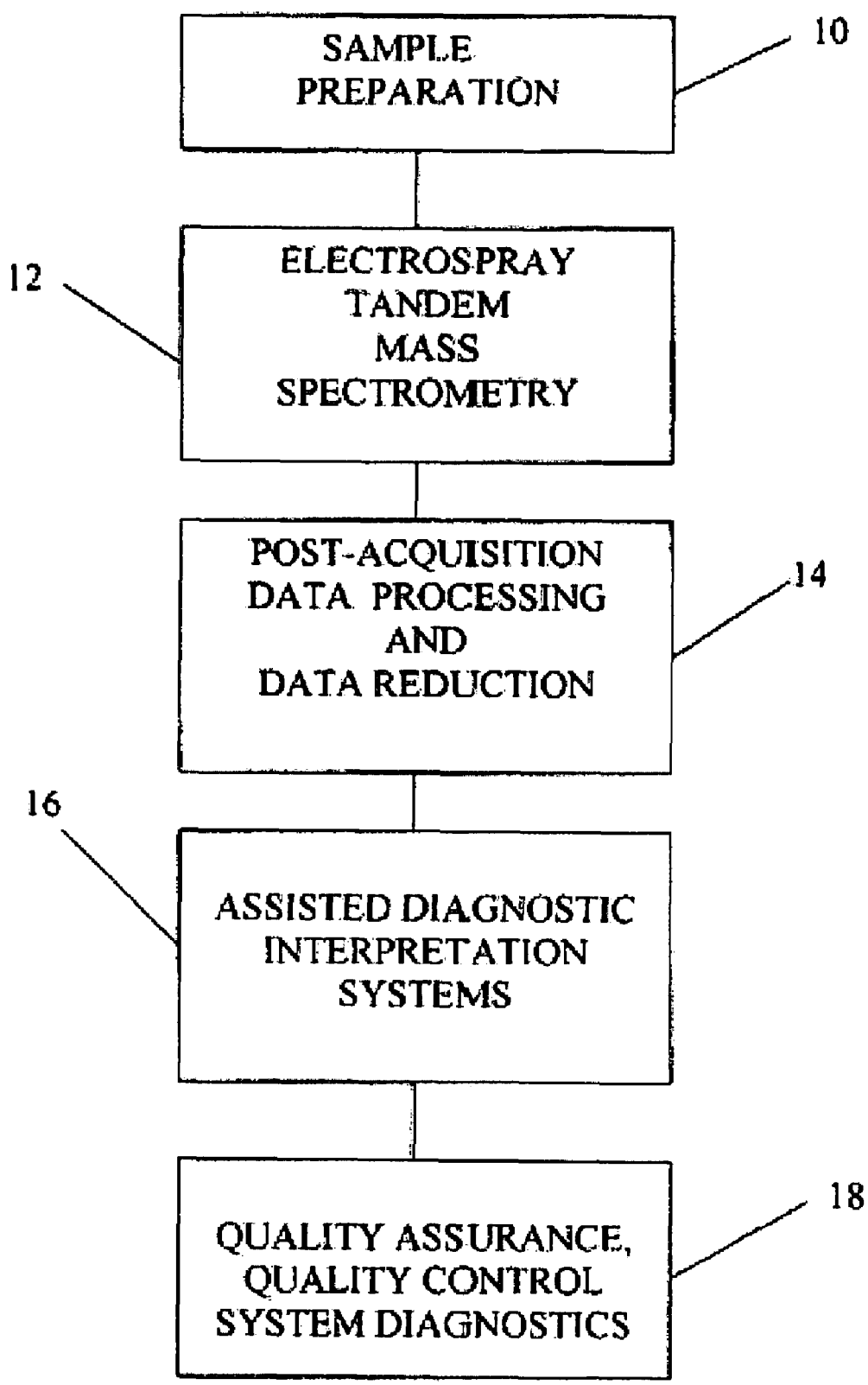
FIG. 1 is a simplified block diagram showing the overall methodology. Five principle processed are correlated from sample preparation to system diagnostics.

FIG. 1 represents an overview of the method of screening newborns in the clinical diagnostic setting involving five main steps, each of which are important for rapid, automated, and accurate sample analysis. Efficient sample preparation 10 is necessary to insure accurate derivatization of the metabolites, and certain additives or internal standards are implemented and important to provide quantitative information for specific components of each sample. After sample preparation 10, the samples are loaded into the electrospray tandem mass spectrometer 12, which implements many automated features to insure the speed and consistency of sample scanning. Data is then acquired and processed to a reduced and organized form as seen in box 14. Values produced from the scan of the mass spectrometer are processed and printed into spreadsheet form to further allow checking of the calculations, a means of assuring accurate number production and quality. Acquired data is then interpreted by an assisted diagnostic interpretation system 16 which integrates the results with the demographic data related to the baby and allows for correlation to a specific disorder based on any noted peaks. The process, working in conjunction with software, allows for data reporting which is a way of monitoring daily output and assisting in necessary decision making for further action, such as follow-up, or re-testing. All spectra data is kept accurate using system diagnostic checks and quality control samples as seen in step 18. To assure diagnostic accuracy and sample quality, periodic system integrity checks and control samples that include specific additives are employed. In combination, the above mentioned steps maximize the rate and quality at which newborn blood samples are screened for metabolic disorders, which is necessary in the clinical setting.

Figure 2:
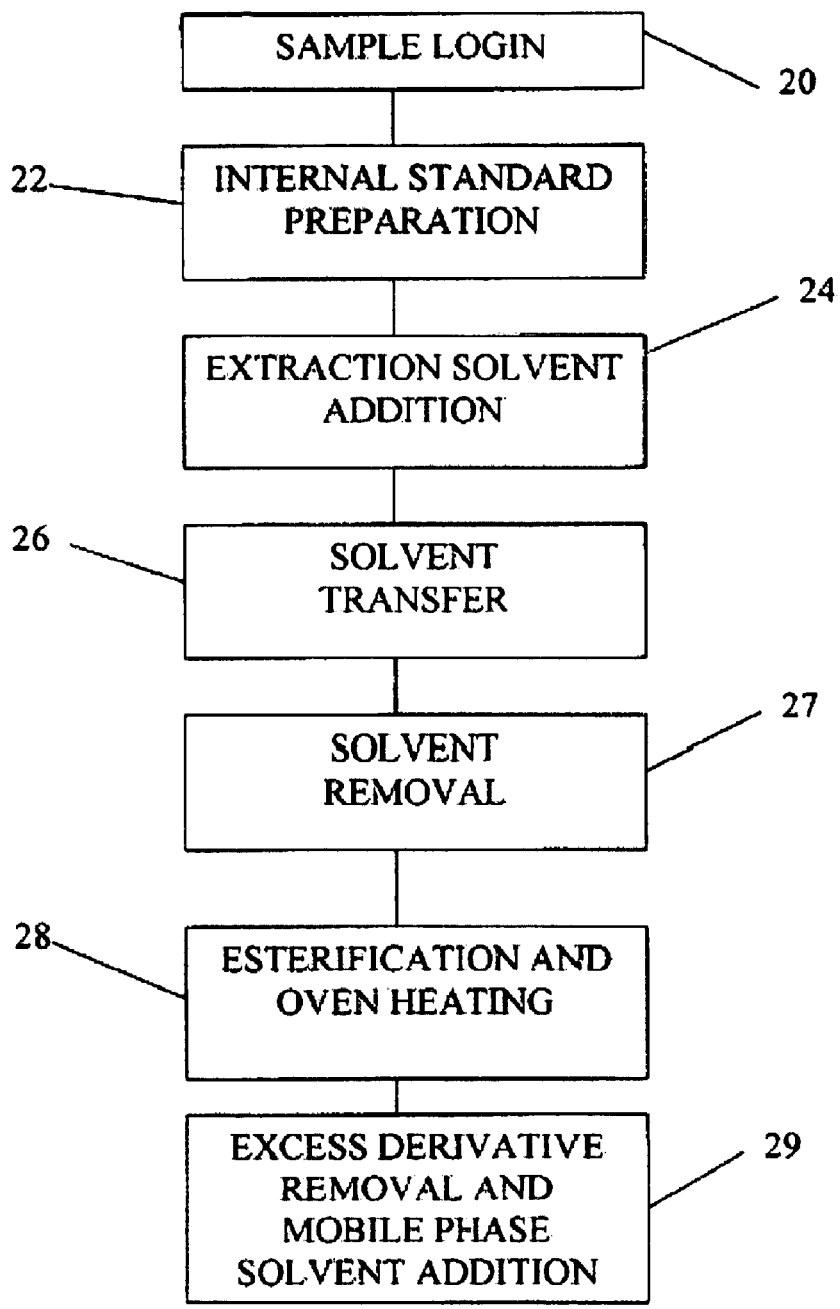
FIG. 2 is a block diagram showing in more detail the steps involved in preparing the sample.

FIG. 2 shows an overview of the sample preparation procedure (step 1 of FIG. 1). An initial sample login 20 is performed by coding each sample, thereby associating the sample to a specific location in a microtiter well. The samples consist of blood spots placed on designated areas of filter paper. The spots are punched with a diameter in the range of 3/16 in. to 1/8 in. and placed into the designated microtiter well. Internal standard preparations 22 are prepared in methanol to produce an extraction solvent, which is added to the dry blood spot in each well. Extraction solvent additions 24 are performed using automated sample handling equipment.

The methanol serves as the solvent extraction medium while the internal standards serve to quantify the metabolites in the dry blood matrix The internal standard preparations 22 comprise an ideal mix of twenty stable isotopes—twelve amino acid standards and eight acylcarnitine/carnitine standards. A list of the amino acid standards can be found in FIG. 2a The left column shows the standard concentrations of the concentrated working stock 20a. The stock solution is diluted 1:100 v/v with methanol to produce concentrations of daily working standards 22a. The concentrations of the daily working standards 22a can be adjusted to analyze two 3/16", two 1/8" or a single 1/8" dried blood spots by adjusting the volume of the extraction solvent additions 24 (FIG. 2) or the concentration of the working stock 20a. The daily working standards 22a serve as both the extraction solvent and the means for internal standardization of the analysis.

Free Carnitine and Acylcarnitine internal standards are listed in FIG. 2b. Again, the left column lists the concentrations of the working stock 20b used in the dilution with methanol 1:100 v/v, to produce the daily working standards 22b. Also, the daily working standards 22b can be adjusted as described above for the blood spot analysis.

Both groups of standards are provided in the extraction medium for the optimum mixed mode scan functions, which maximize metabolite detection. The metabolite groups detected include the .alpha.-amino acids—alanine, phenylalanine, tyrosine, glutamic acid, ornithine, citrulline, arginine—and the carnitines—free carnitine, acylcarnitines, acetylcarnitine, octanoylcarnitine, palmitoylcarnitine.

Now following FIG. 2, after extraction solvent addition 24, the solvent is transferred at step 26 to a plate, or microtiter plate, having rounded-bottom wells where the solvent is removed using a nitrogen drying system at step 27. The blood extract then undergoes esterification and is chemically modified and heated at step 28 to become a derivative. Excess derivative is removed at step 29 and a mobile phase solvent is added using an automated sample handling system. Plate seals retard any solvent evaporation.

Figure 3:
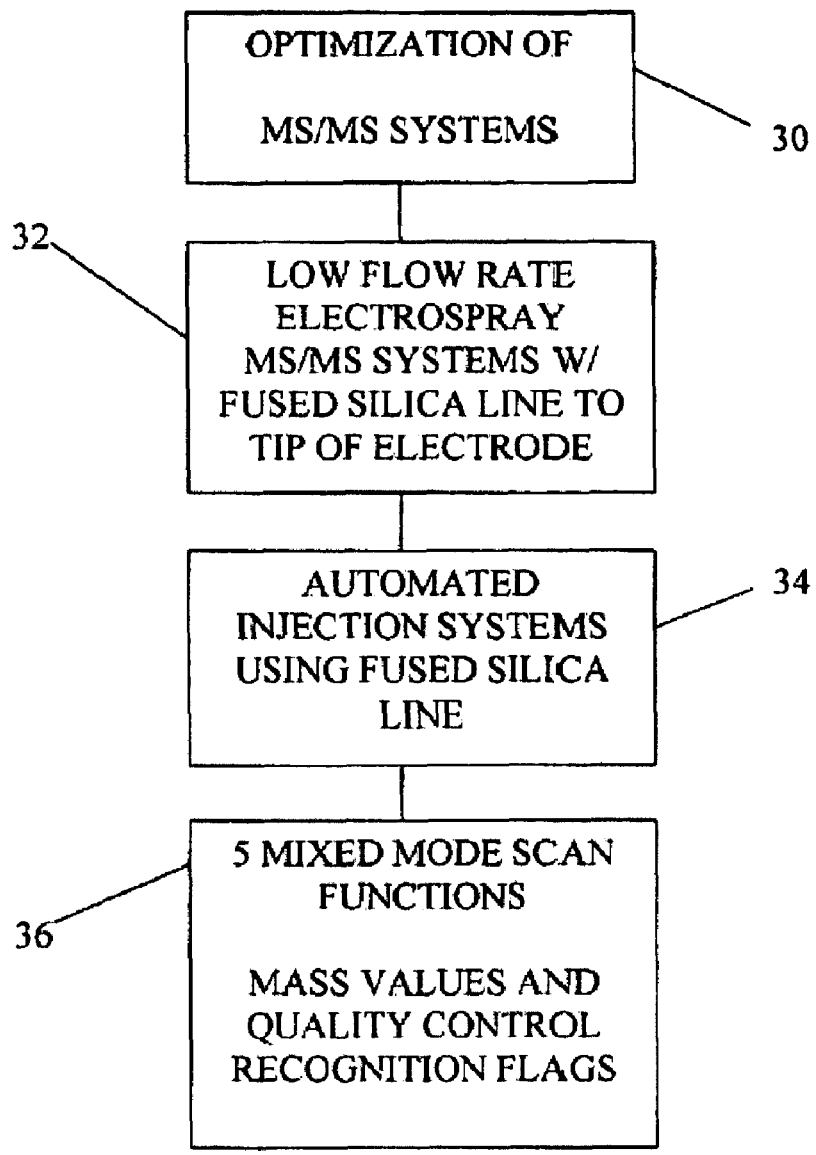
FIG. 3 is a block diagram showing in more detail the steps involved in the automated use of an electrospray tandem mass spectrometer to include the use of proper scan functions to maximize accurate output.

FIG. 3 shows the steps involved after the sample is prepared and standards are included and made ready for introduction into the automated electrospray tandem mass spectrometer. Optimization of the MS/MS systems 30 is achieved by using a tuning solution, and the electrospray MS/MS system 32 is a low flow rate system employing the use of a fused silica line displaced to the tip of the electrode. Automated injection systems 34 use the fused silica line to directly connect the injector to electrode tip to minimize dead space. The scans implemented to detect the necessary fragments of the ions consist of five mixed-mode scan functions 36 for maximizing metabolite and quality assurance information. The mixed-mode scan functions 36 include free carnitine MRM, acetylcarnitine MRM, fill scan acylcarnitine, fill scan amino acids, and basic amino acid MRM, whereas a full scan covers a wider range of mass to charge ratios, thereby a wider range of peaks can be compared. Each peak corresponds to a concentration or threshold number and compared to a known upper or lower threshold.

Examples of the values of the thresholds can be seen in FIG. 3a. It should be understood that all sample values necessary in metabolic error determination or quality assurance falling above or below a certain threshold are flagged, or identified, for diagnostic purposes, re-testing, or other clinical decision making.

Figure 3B:
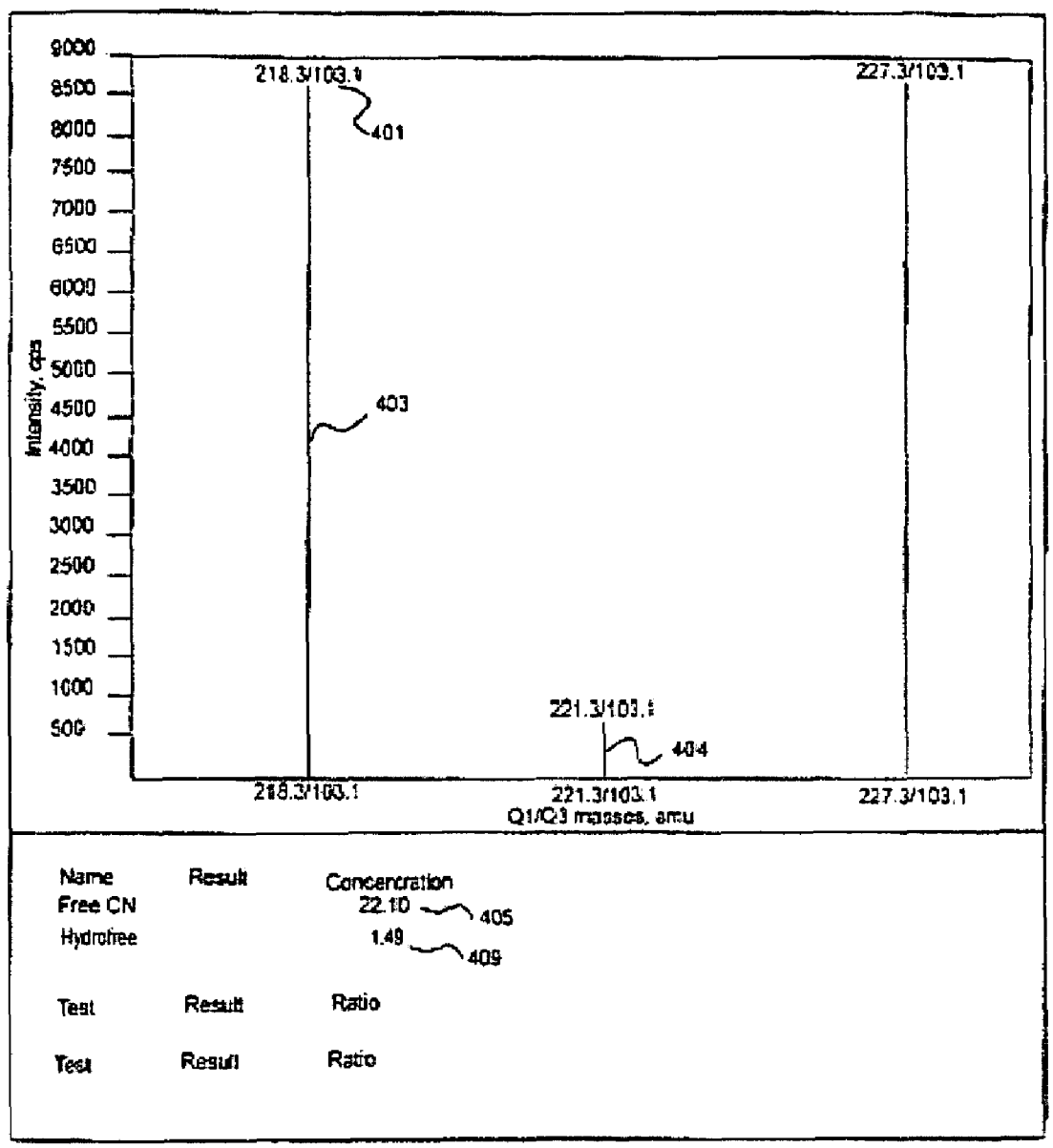
FIG. 3b is an example of a Free Carnitine MRM scan, showing the pertinent peaks and values for quality assurance.

FIG. 3b demonstrates a Free Carnitine MRM implementing quality assurance. An MRM is a scan for a particular compound showing dual masses 401 (parent mass and daughter mass respectively). A first peak 403 is detected as the free carnitine fragments. The resulting concentration of Free Carnitine 405 is then given Quality is assured in this scan by looking at the $d_3$ free CN (deuterium 3 carnitine) peak 404 which comes from the hydrolysis of $d_3$ labeled acylcarnitines. The resulting "hydrofree" concentration value 409 is a quality assurance flag for acylcarnitine hydrolysis and is also a correction for true concentrations of Free Carnitine 405.

Figure 3C:
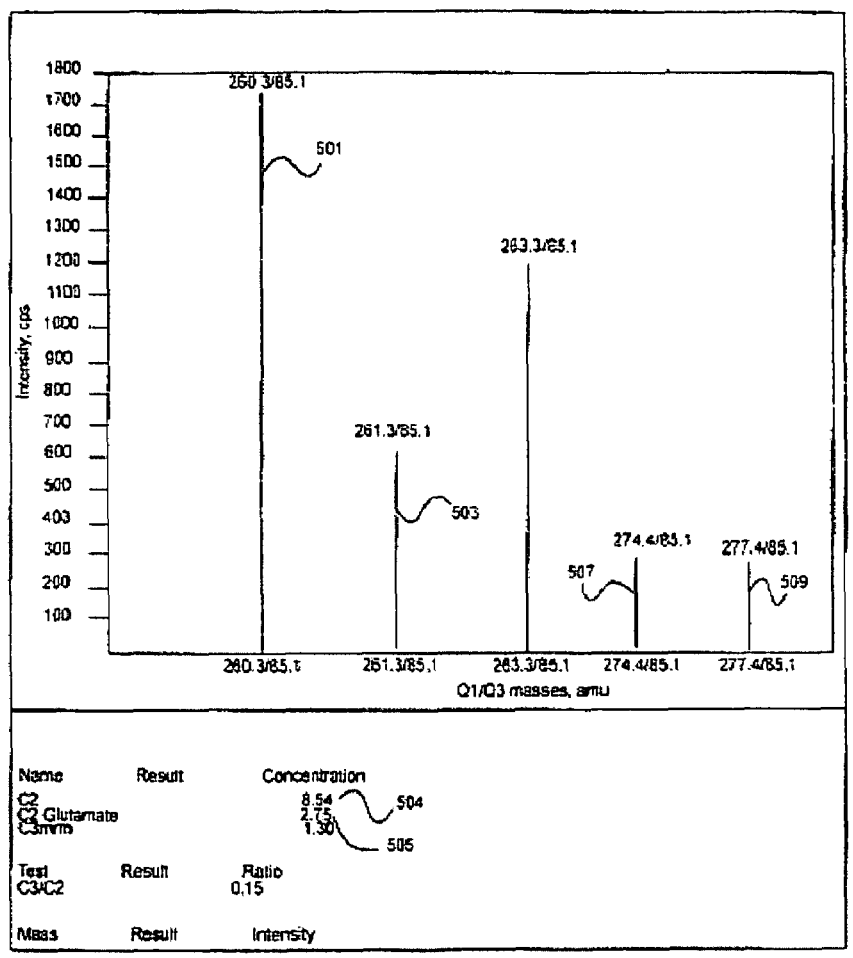
FIG. 3c is an example of an Acetylcarnitine MRM scan, showing the pertinent peaks and values for quality assurance.

FIG. 3c demonstrates an Acetylcarnitine MRM. Peak 501 is the acetylcarnitine (acetylCN) peak and peak 503 is a quality assurance (QA) peak manifesting the hydrolysis of glutamate. The resulting glutamate concentration 505 shows the amount of interference from a glutamate, which is corrected for in the acetylCN concentration 504 determination Other QA checks for propionyl CN are implemented in this scan as duplicate peaks 507 and 509.

Figure 3D:
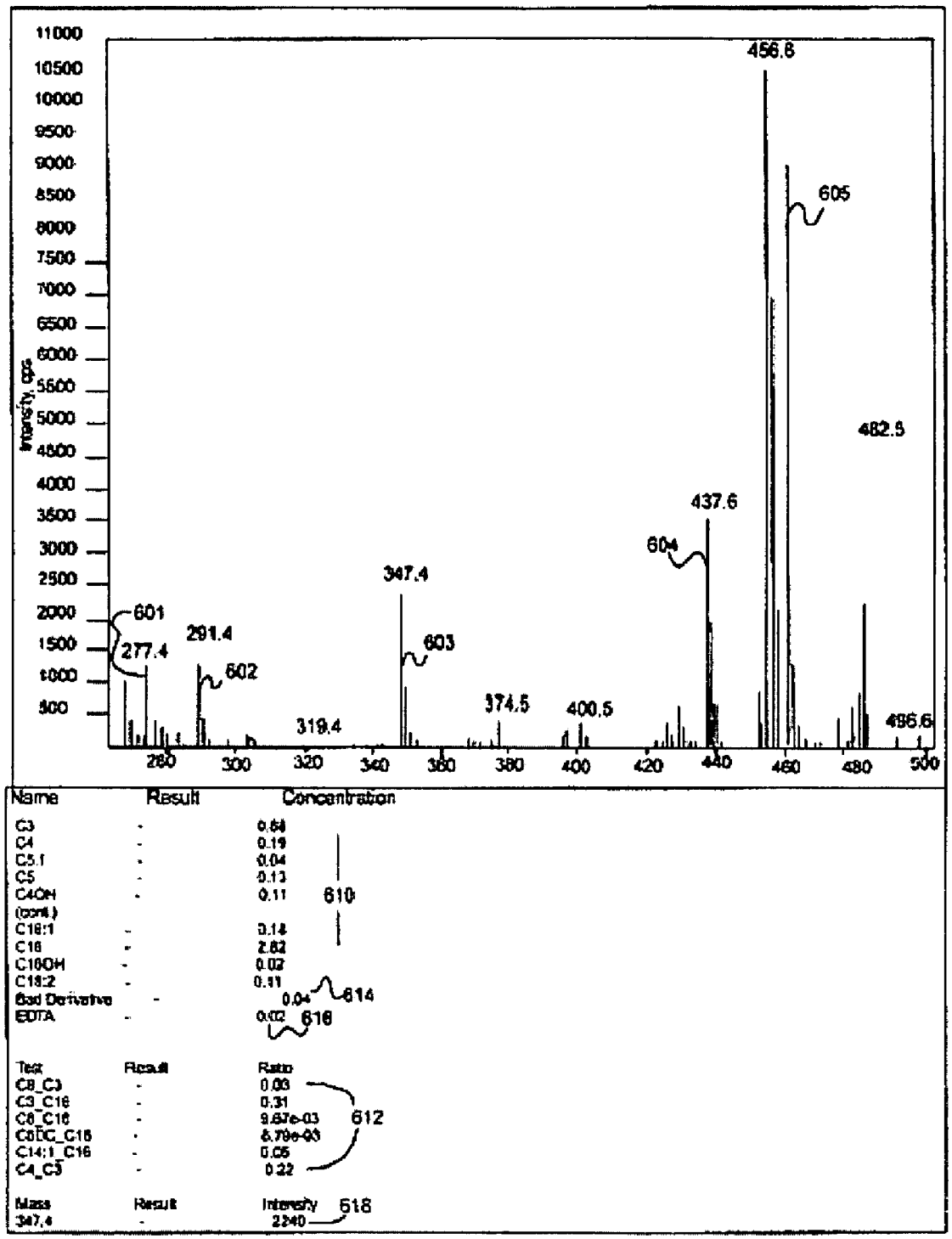
FIG. 3d is an example of a full scan Acetylcarnitine profile, showing the pertinent peaks and values for quality assurance.

A profile of the Acylcarnitine full scan is shown in FIG. 3d. Added internal standards are fragmented and revealed as peaks 601, 602, 603, 604, 605. A list of the concentrations of the detectable metabolites 610 is then provided as well as the molar ratios 612. A QA test is included in this scan as a bad derivative value 614 which stems from any peak found around a m/z, amu value of 403. The bad derivative value 614 would reveal poor sample preparation if elevated. An EDTA QA flag 616 is also implemented to reveal sample collection method. Elevated values of the EDTA QA flag 616 manifest samples drawn from tubes rather than heel pricks, or reveal lengthy preservation maintenance.

Another QA method is used in this scan, revealed by an intensity value 618. An elevated intensity value shows the sample was scanned with adequate sensitivity. If the intensity value 618 is too low, the sample will be flagged (noted), and the sample may be re-tested depending on the protocol.

Figure 3E:
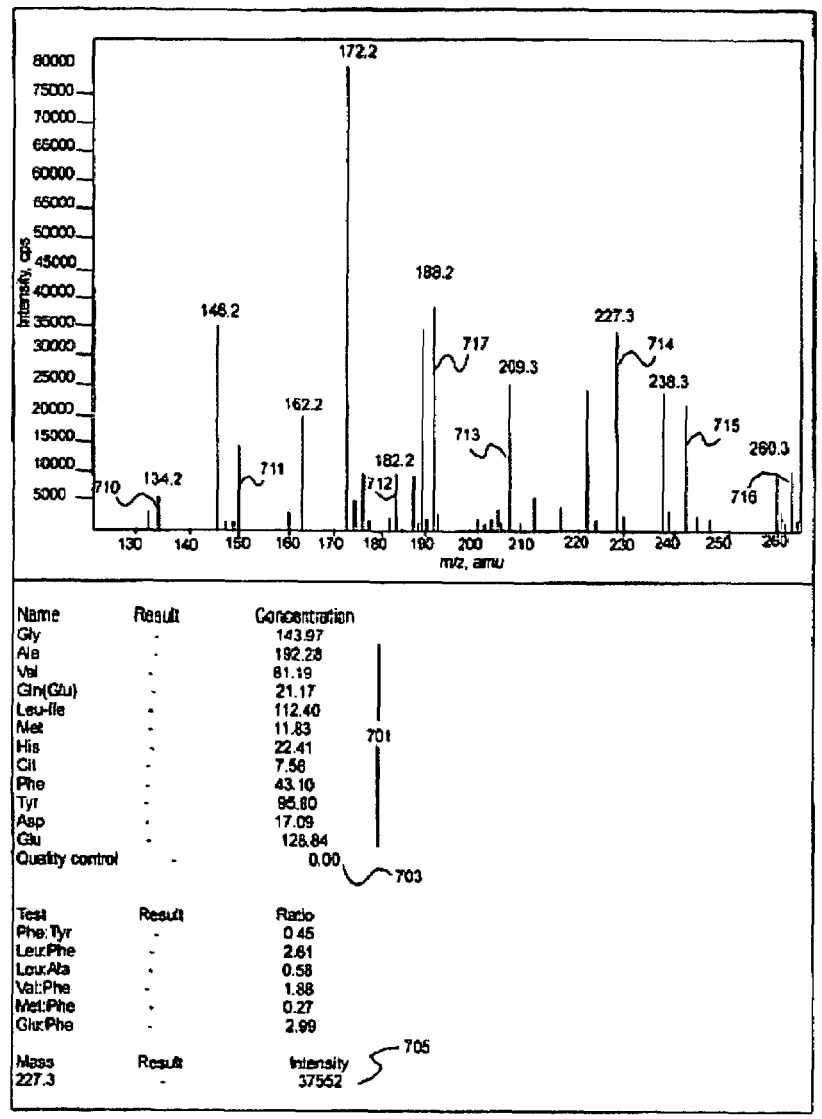
FIG. 3e is an example of a full scan Amino Acid profile, showing the pertinent peaks and values for quality assurance.

FIG. 3e is an example of a full scan Amino Acid analysis. Amino acids in the internal standards fragment and are shown as peaks 710, 711, 712, 713, 714, 715, 716, 717. Amino Acid concentration values 701 are listed, along with a QA flag value 703 at around a m/z, amu value of 165. The QA flag value 703 would most likely be produced from the addition of $^2H_3$-Serine, which would be added in a sample to manifest proper detection of compounds normally not found in a routine sample, as Serine is an amino acid not included in the list of amino acids relevant to any disorders. An intensity flag 705 is also implemented to show adequate sensitivity in detection.

Figure 3F:
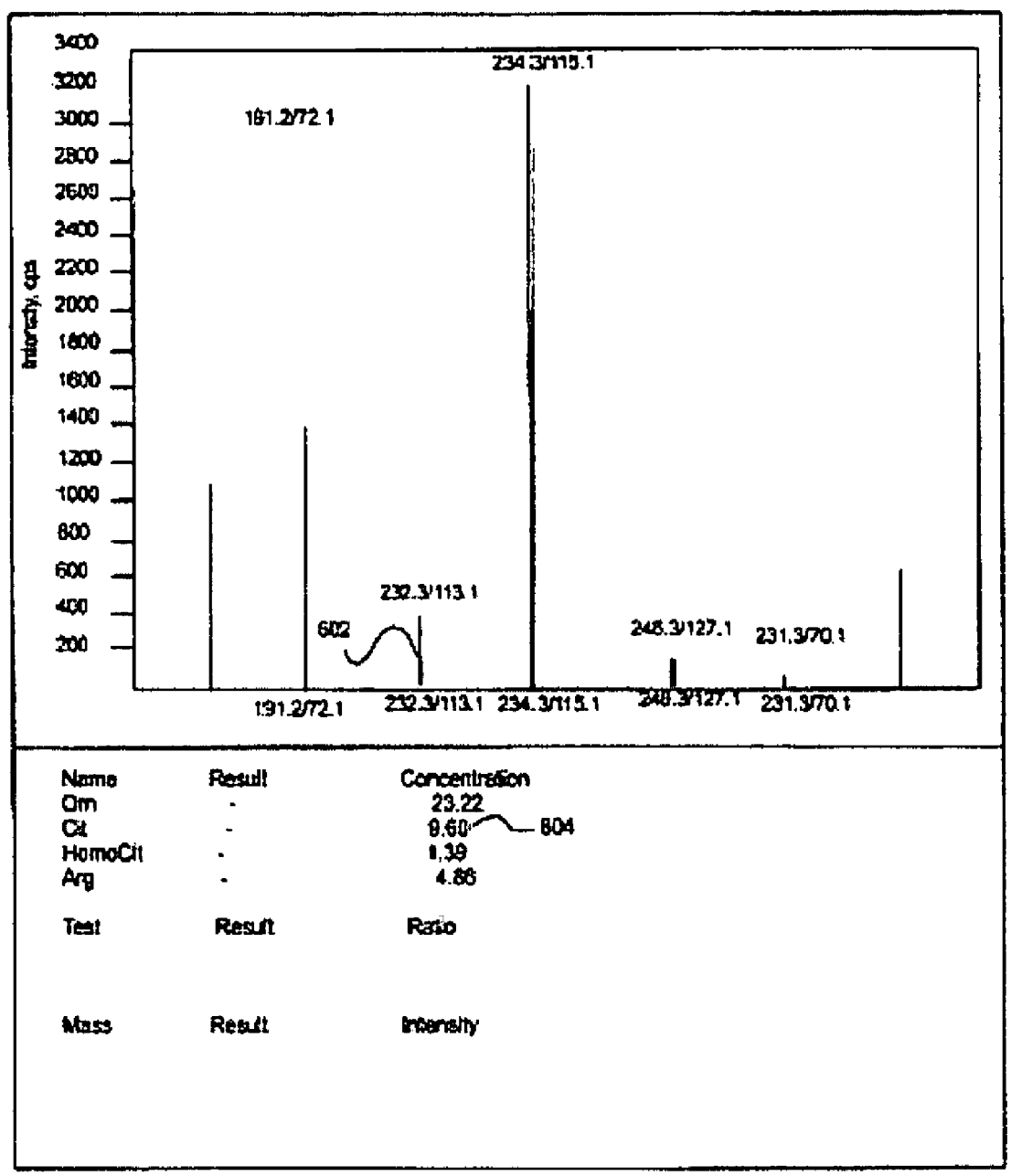
FIG. 3f is an example of a basic Amino Acid MRM scan, showing the pertinent peaks and values for quality assurance.

FIG. 3f is an example of a basic Amino Acid MRM. The QA flag occurs at peak 802, and the scan includes duplicate Citrulline analysis 804, normally peaking around a m/z value of 215 and 232.

Figure 4:
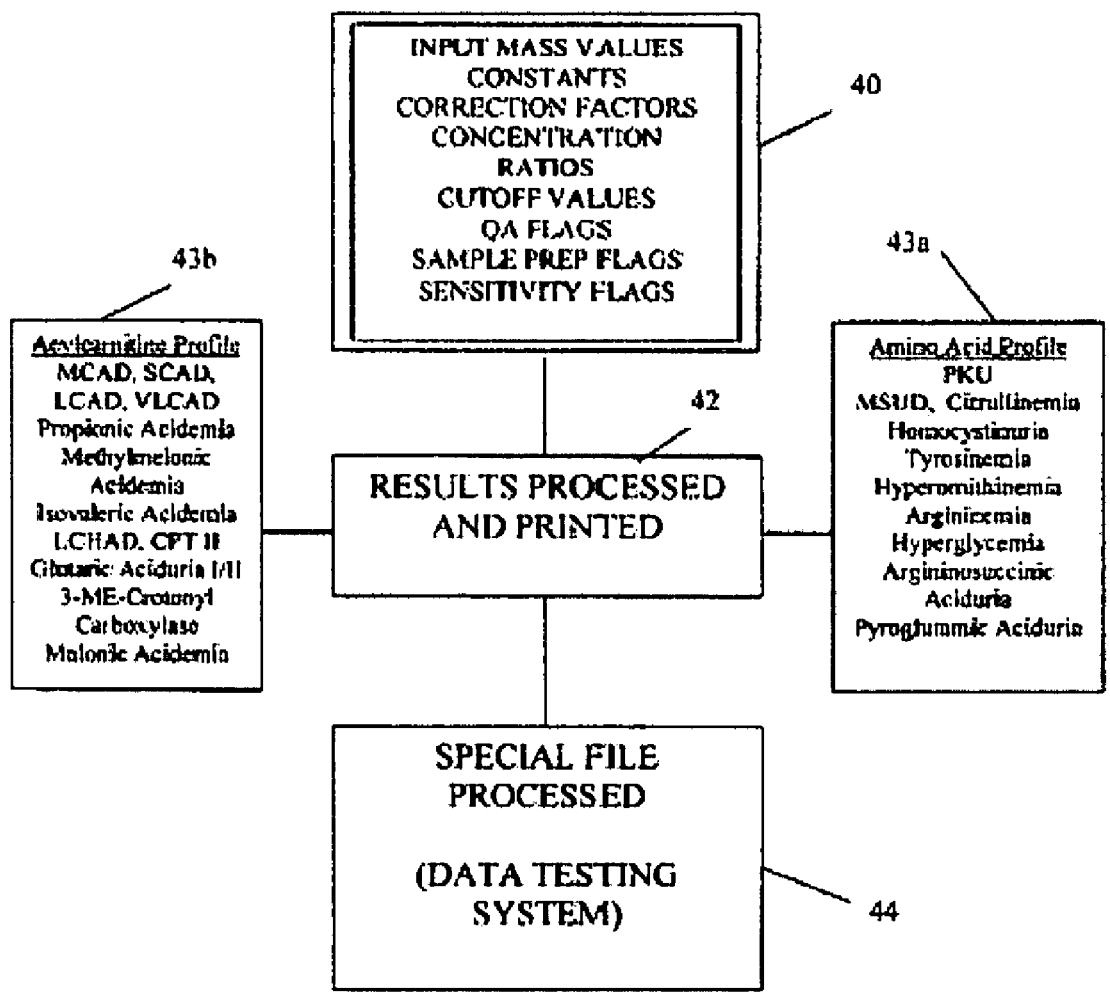
FIG. 4 is a block diagram showing in more detail the steps involved in processing the data after acquisition of the values, which have been produced from the spectrometer.

FIG. 4 describes the processing of the data acquired from the scan functions used for the mass spectrometer. Step 40 is the input of all mass values, constants for concentration calculations, correction factors for extraction efficiency, ratios of concentration data, and cut-off values. Quality assurance flags, sample preparation flags, and sensitivity flags are also inputted. The flags include the above described peaks, intensity values, bad derivative values, and EDTA values, and are important because they reveal whether or not the samples are contaminated or drug-ridden, and they are very telling of how the samples were contained, or from where the samples were drawn. Also, they assist in maintaining instrument accuracy and consistency. The results are processed and printed for step 42. The scan functions described for FIGS. 3a-3e can detect multiple diseases based on the fragments of the metabolites detected The revealing peaks will eventually lead to the profiles noted in boxes 43a and 43b. The profiles may include the noting of peaks picked up using the quality assurance or quality control standards as well.

Figure 5:
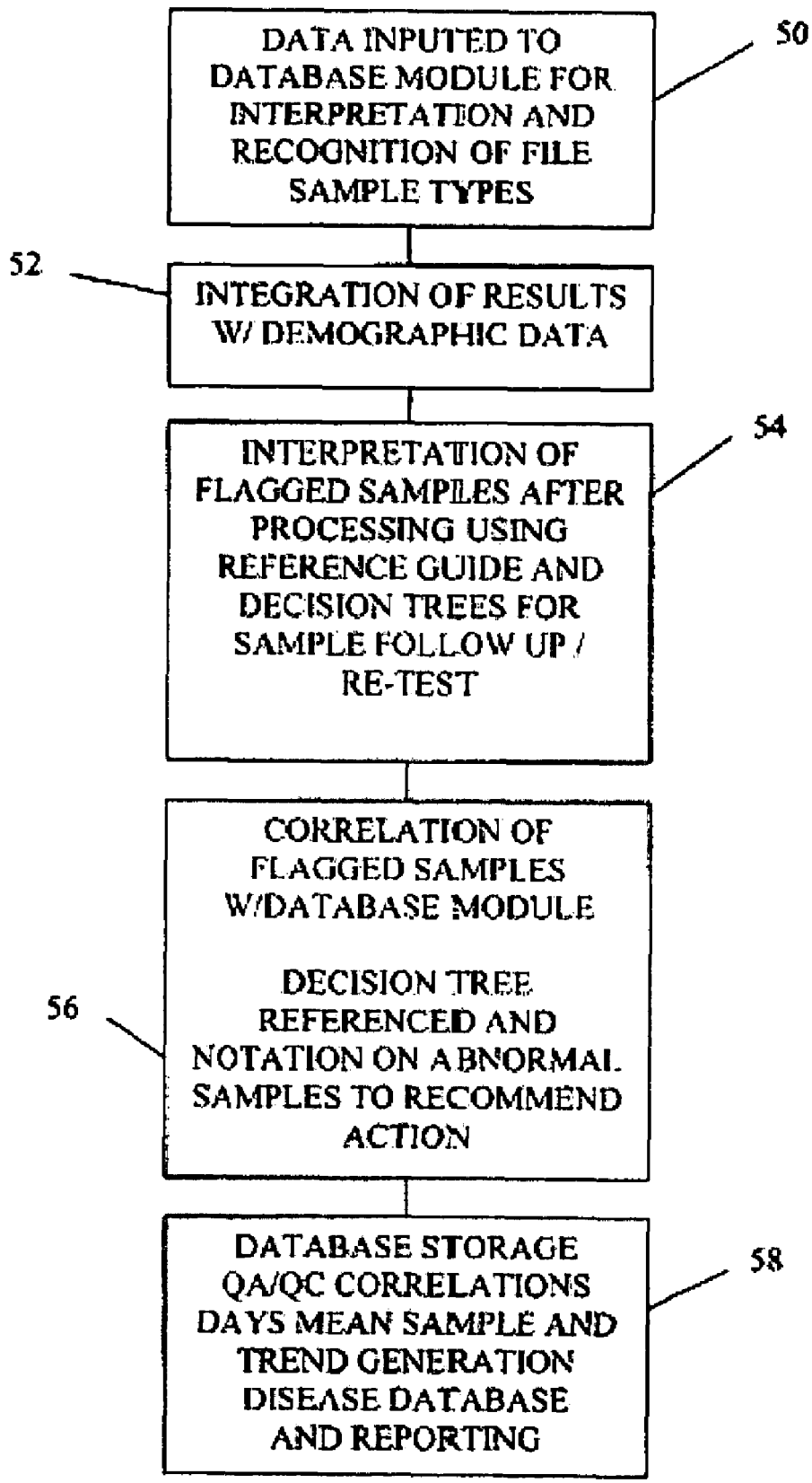
FIG. 5 is a block diagram showing in more detail the steps involved in interpreting the data as it relates to demography and decision making.

FIG. 5 shows the steps involved in interpreting the organized data. The spreadsheet data is inputted to a database module for recognition of the file and sample types. As seen in step 50, the data is interpreted so parameters can be assigned to the particular sample, and the results given. The results are then integrated in step 52 with demographic data of the newborn. The demographics may include age, type of specimen, or other notation such as whether or not the baby is premature, etc. Samples that show an abnormality, or seem to show a revealing peak, are flagged to be interpreted using a reference guide and decisions are made on the next course of action as step 54. Referencing the decision tree and recommending action would be the next step as step 56. The flagged samples are correlated with the database module used to distinguish abnormal peaks, and a decision to re-test or diagnosis is made. In step 58, as a measure of quality assurance and quality control, the days mean sample and trend generation is recorded to follow the statistical occurrences of diseases, and to maintain high-throughput sampling. This includes automated data reporting and internet communication reporting.

Figure 6:
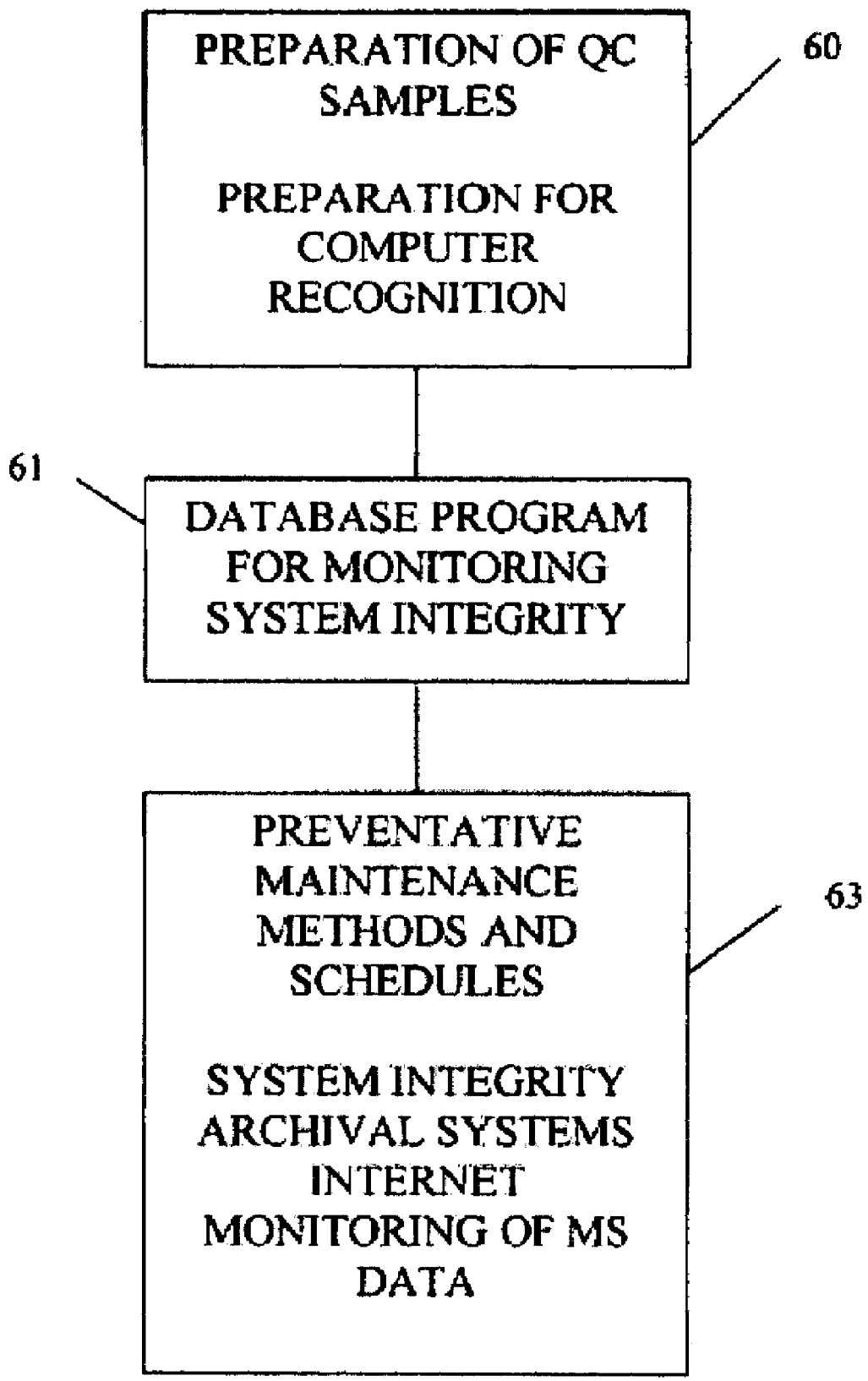
FIG. 6 is a block diagram showing in more detail the steps involved in monitoring system diagnostics and implementing quality controls.

FIG. 6 shows the steps involved in further maintaining quality assurance using quality control samples and maintaining system integrity. Quality control samples are prepared as step 60. The samples consist of QA blood spots and liquids prepared as unlabeled standards at the same concentrations as the internal standards, and scanned The control blood standards implemented in this step 60 consist of hemolyzed blood, EDTA, and $^2H_3$-Serine, or some other recognized marker. These are run and compared to standards that consist of hemolyzed blood, EDTA, $^2H_3$-Serine, and one of the twenty compounds that are the same as those used in the internal standards, but unlabeled. The computer is properly set up to recognize and interpret the results. Another step in maintaining quality assurance is provided as step 61. Systems are monitored in a database program to detect changes in system integrity or sensitivity. A final step in maintaining system diagnostics is included as step 63. Maintenance methods and schedules are constantly followed and monitored through archival systems and via the Internet through ongoing monitoring of mass spectrometry data.

I claim:

1. An internal standard preparation comprising $^2H_9$-carnitine, $^2H_3$-acetylcarnitine, $^2H_3$-propionylcarnitine, $^2H_3$-butyrylcarnitine, $^2H_9$-isovalerylcarnitine, $^2H_3$-octanoylcarnitine, $^2H_9$-myristoylcarnitine, and $^2H_3$-palmitoylcarnitine.

2. The internal standard preparation of claim 1, wherein said preparation is a methonalic solution.

3. The internal standard preparation of claim 1, wherein said preparation is a solution and said $^2H_9$-carnitine is present at a concentration of about 0.76 nmol/l.

4. The internal standard preparation of claim 1, wherein said preparation is a solution and said $^2H_3$-acetylcarnitine is present at a concentration of about 0.19 nmol/l.

5. The internal standard preparation of claim 1, wherein said preparation is a solution and said $^2H_3$-propionylcarnitine is present at a concentration of about 0.04 nmol/l.

6. The internal standard preparation of claim 1, wherein said preparation is a solution and said $^2H_3$-butyrylcarnitine is present at a concentration of about 0.04 nmol/l.

7. The internal standard preparation of claim 1, wherein said preparation is a solution and said $^2H_9$-isovalerylcarnitine is present at a concentration of about 0.04 nmol/l.

8. The internal standard preparation of claim 1, wherein said preparation is a solution and said $^2H_3$-octanoylcarnitine is present at a concentration of about 0.04 nmol/l.

9. The internal standard preparation of claim 1, wherein said preparation is a solution and said $^2H_9$-myristoylcarnitine is present at a concentration of about 0.04 nmol/l.

10. The internal standard preparation of claim 1, wherein said preparation is a solution and said $^2H_3$-palmitoylcarnitine is present at a concentration of about 0.08 nmol/l.

11. The internal standard preparation of claim 1, wherein at least two of said $^2H_3$-propionylcarnitine, $^2H_3$-butyrylcarnitine, $^2H_9$-isovalerylcarnitine, $^2H_3$-octanoylcarnitine, and $^2H_9$-myristoylcarnitine are present in about equal amounts.

12. The internal standard preparation of claim 1, wherein the preparation includes an amount of $^2H_3$-palmitoylcarnitine that is about double that of at least one of $^2H_3$-propionylcarnitine, $^2H_3$-butyrylcarnitine, $^2H_9$-isovalerylcarnitine, $^2H_3$-octanoylcarnitine, and $^2H_9$-myristoylcarnitine.

13. A composition that includes the internal standard preparation of claim 1 in combination with an extract from a blood sample.

* * * * *